(12) United States Patent
Tsang et al.

(10) Patent No.: US 7,131,318 B2
(45) Date of Patent: Nov. 7, 2006

(54) VISCOMETER

(75) Inventors: Charles Y. Tsang, Vancouver (CA);
Gordon S. Y. Chiu, Richmond (CA);
Jonathan D. Gosling, Dublin (IE);
Stephen J. Gosling, Essex (GB)

(73) Assignee: Phase PSL Instrument Inc., Richmond (CA)

( * ) Notice: Subject to any disclaimer, the term of this patent is extended or adjusted under 35 U.S.C. 154(b) by 217 days.

(21) Appl. No.: 10/711,592

(22) Filed: Sep. 28, 2004

(65) Prior Publication Data

US 2006/0065044 A1 Mar. 30, 2006

(51) Int. Cl.
*G01N 11/06* (2006.01)
(52) U.S. Cl. .................................... 73/54.07
(58) Field of Classification Search ............... 73/54.07, 73/54.16
See application file for complete search history.

(56) References Cited

U.S. PATENT DOCUMENTS

| | | | | |
|---|---|---|---|---|
| 2,095,282 A | * | 10/1937 | Payne | 73/54.04 |
| 2,791,902 A | * | 5/1957 | Jones, Jr. | 73/54.09 |
| 3,024,642 A | * | 3/1962 | Jones, Jr. | 73/54.43 |
| 3,680,362 A | * | 8/1972 | Geerdes et al. | 73/54.13 |
| 3,686,931 A | * | 8/1972 | Norcross | 73/54.16 |
| 3,798,960 A | * | 3/1974 | Glass | 73/54.05 |
| 3,895,513 A | * | 7/1975 | Richardson | 73/54.07 |
| 4,067,230 A | * | 1/1978 | Ball | 73/54.01 |
| 4,466,275 A | * | 8/1984 | Thone | 73/54.16 |
| 4,554,821 A | | 11/1985 | Kiesewetter et al. | |
| 4,616,503 A | | 10/1986 | Plungis et al. | |
| 4,723,442 A | | 2/1988 | Manning et al. | |
| 5,327,778 A | | 7/1994 | Park | |
| 6,470,736 B1 | * | 10/2002 | Price | 73/54.04 |
| 6,584,830 B1 | | 7/2003 | Long | |

* cited by examiner

*Primary Examiner*—Daniel S. Larkin
*Assistant Examiner*—John Fitzgerald
(74) *Attorney, Agent, or Firm*—John J. Elnitski, Jr.

(57) ABSTRACT

A viscometer including a thermal block, a thermo device to control temperature of the thermal block, a temperature sensor to sense temperature of the thermal block, a capillary tube embedded in the thermal block such that the capillary tube is in thermal contact with the thermal block, an entrance tube connected to the capillary tube and embedded in the thermal block, a velocity tube connected to the capillary tube and embedded in the thermal block and at least two flow sensors aligned along the velocity tube adapted to measure velocity of the test specimen in the velocity tube.

29 Claims, 11 Drawing Sheets

VISCOMETER

BACKGROUND

Viscosity is a measure of resistance to flow for a liquid. Higher viscosity means a stronger resistance to flow. There are two types of viscosity measurements. The first is dynamic viscosity, which is a measure of the internal resistance to flow of a liquid. The second is kinematic viscosity, which is the liquid's resistance of flow under the force of gravity. Kinematic viscosity is defined as dynamic viscosity divided by density of the liquid.

Viscosity is an important property for liquid, especially for petroleum liquids such as fuels and lubricants and is often specified in the trading of petroleum products. Also, the manner in which the measurement is conducted is specified in test standards such as the ASTM D445 standard. Inherent to the ASTM D445 standard is an expectation of precision. A slight deterioration in precision can have a profound impact on the cost of producing petroleum products, especially lubricants. For example, a one percent (1%) error in the measurement of kinematic viscosity can lead to a one million dollar per year of loss revenue for a large lubricant blending plant. Thus, it is well appreciated in the industry that tight control on the measurement precision of viscosity is critical to the profitability of manufacturing plants.

ASTM D445 specifies the apparatus and procedures for measuring the kinematic viscosity of petroleum liquids. It involves the use of a glass capillary system. In essence, a fixed amount of liquid sample is allowed to flow under gravity through a glass viscometer submerged in a constant temperature liquid bath, and the time taken to flow between timing marks is used to calculate the resultant viscosity.

There are numerous challenges in practicing the ASTM D445 standard. The apparatus is typically large, heavy, and difficult to transport. While a glass capillary column is only about one foot in length itself, the entire system incorporating a liquid bath can be substantially larger. The capillary must be immersed in a constant temperature liquid bath, typically set between forty and one-hundred degrees Celsius. The liquid bath wall is made of glass to allow visual observation of the meniscus of the sample liquid.

Apart from taking up a lot of space in the laboratory, the glass capillary is fragile, and because of its often elaborate construction in accommodating various bends and restrictions in the flow path, difficult to clean. Cleaning is a critical part of the viscosity measurement procedure because a slight contamination of the sample by residuals from the previous sample or cleaning agent could have a significant impact on subsequent viscosity measurement results. Cleaning is also the most time-consuming part of the whole testing process, as it requires multiple rinsing of the capillary with solvents followed by drying between each rinsing. Viscous samples such as lubricants and heavy fuel oils are more difficult to clean than less viscous materials such as jet fuels and diesels. Moreover, the liquid bath is a potential fire and burn hazard since the glass wall is vulnerable to breakage with its large volume of hot liquid when operated at high temperatures. There are also technical challenges in maintaining stable temperature in the liquid bath and in relying on human operators to precisely measure the flow time of liquid in the capillary using stopwatches.

There have been attempts by different systems to overcome the disadvantages of the ASTM D445 standard. Most of these attempts have not received universal acceptance due to their own unique disadvantages, such as a lack of precision in the test results; or mechanical complexity of the machines required to complete the test. Most of them solely rely on gravity to drive the flow of the liquid column. They do not include any provision for cleaning the capillary tube at the end of a test. In fact, a lot of them promote the idea of using a disposable tube. To achieve the precision of less than one percent (1%) typically required of measured value for petroleum products, each capillary tube must be carefully calibrated. Calibration means that the tube must be tested repeatedly for multiple standard samples. The tube must be clean prior to each test to avoid contamination from previous sample(s). Therefore cleaning is a very important aspect for a calibrated viscometer. Some of the system's measurement of flow time relies on the detection of the trailing meniscus at the end of the liquid column. This will not be suitable for opaque samples which occur frequently in petroleum samples. Opaque sample can soil, stain, or otherwise leave a smear on the walls of the tubing, rendering detection of the passage of the trailing meniscus unclear or even impossible to observe.

It is an object of the present invention to provide a compact device that is capable of determining viscosity of liquids in a precise, yet convenient manner.

It is an object of the present invention to provide a compact device that reduces cleaning and cleaning time.

SUMMARY OF THE INVENTION

A viscometer including a thermal block, a thermo device to control temperature of the thermal block, a temperature sensor to sense temperature of the thermal block, a capillary tube embedded in the thermal block such that the capillary tube is in thermal contact with the thermal block, an entrance tube connected to the capillary tube and embedded in the thermal block, a velocity tube connected to the capillary tube and embedded in the thermal block and at least two flow sensors aligned along the velocity tube adapted to measure velocity of the test specimen in the velocity tube.

DETAILED DESCRIPTION

The present invention is a viscometer. The viscometer of the present invention is a smaller, more robust device than currently available. The viscometer of the present invention is amenable to automation with minimal operator involvement. The viscometer of the present invention allows the measurement of both the dynamic and kinematic viscosities in one test sequence. The viscometer of the present invention also allows convenient change in the shear rate for characterizing non-Newtonian liquids, which is not available in devices setup for the ASTM D445 standard. The viscometer of the present invention uses a thermal conductive block to replace the liquid thermal bath for maintaining temperature of the capillary tube. Because of the high thermal density and conductive nature of the thermal conductive block, the viscometer of the present invention is significantly more compact and the hazards related to a high temperature liquid bath are also eliminated.

The viscometer includes a capillary tube in which a test specimen flows under an external driving force through the capillary tube. There is a means of changing the external driving force to effect a change in shear rate. The viscometer includes multiple detectors which monitor the velocity of the flow of the test specimen. The viscometer includes means of changing the test specimen temperature and measuring the test specimen temperature. The viscometer includes a means of introducing cleaning media at the end of a test cycle to clean the capillary tube. Finally, a microprocessor-based electronic system can be used to analyze the information and output suitable messages concerning viscosity of the test specimen. The operational concept of the viscometer is to measure flow velocity of the test specimen under a fixed amount of force of the drive pressure. Assuming Newtonian flow, the Hagen-Poiseuille equation states the relation between dynamic viscosity $\mu$ and flow velocity V is $\mu=32LV/\Delta PD^2$. Where L and D are the length and internal diameter of the capillary system respectively, and $\Delta P$ is the drive pressure.

Figure 1:
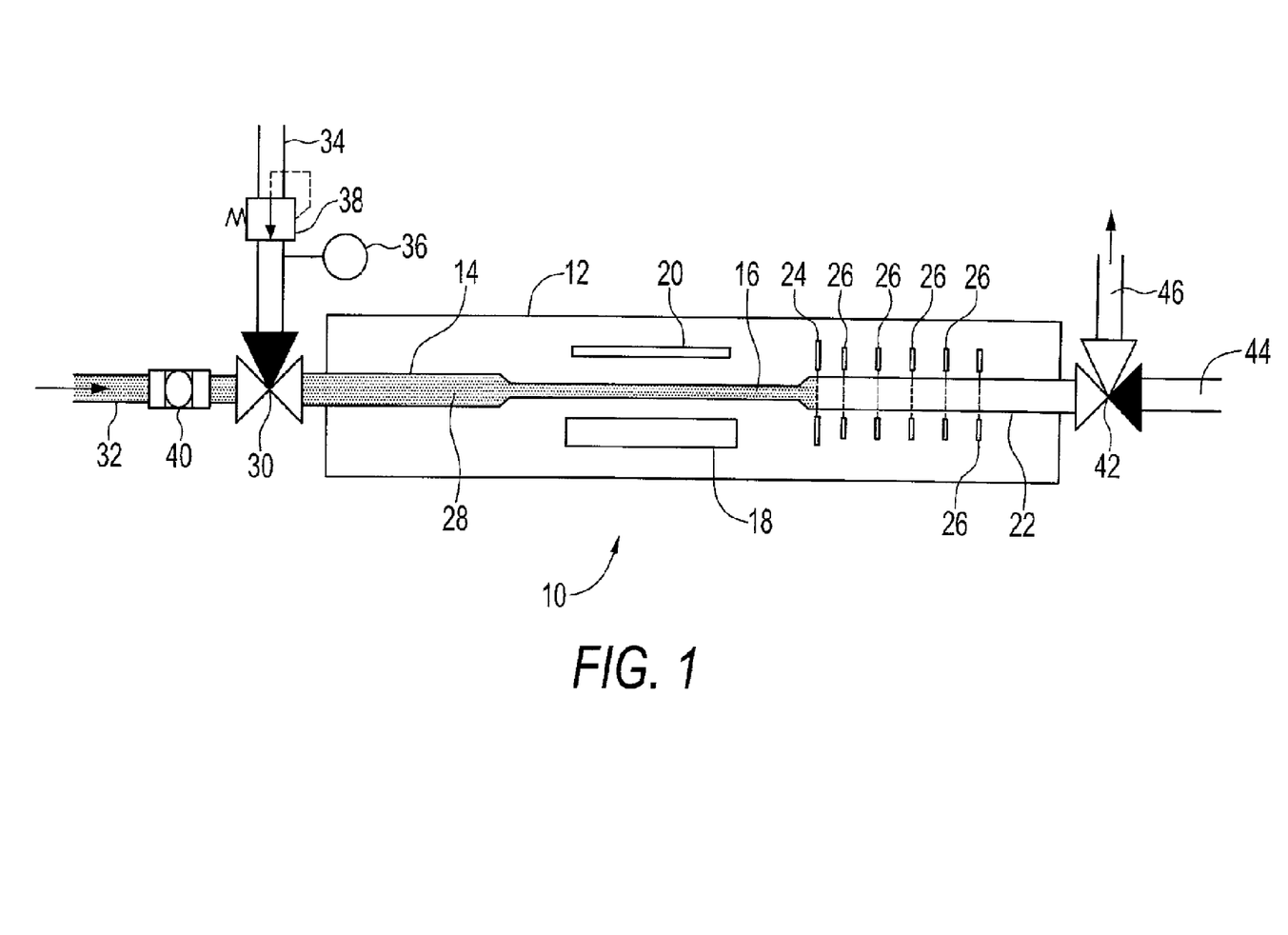
FIG. 1 is a side view of a viscometer according to the present invention.
Figure 2:
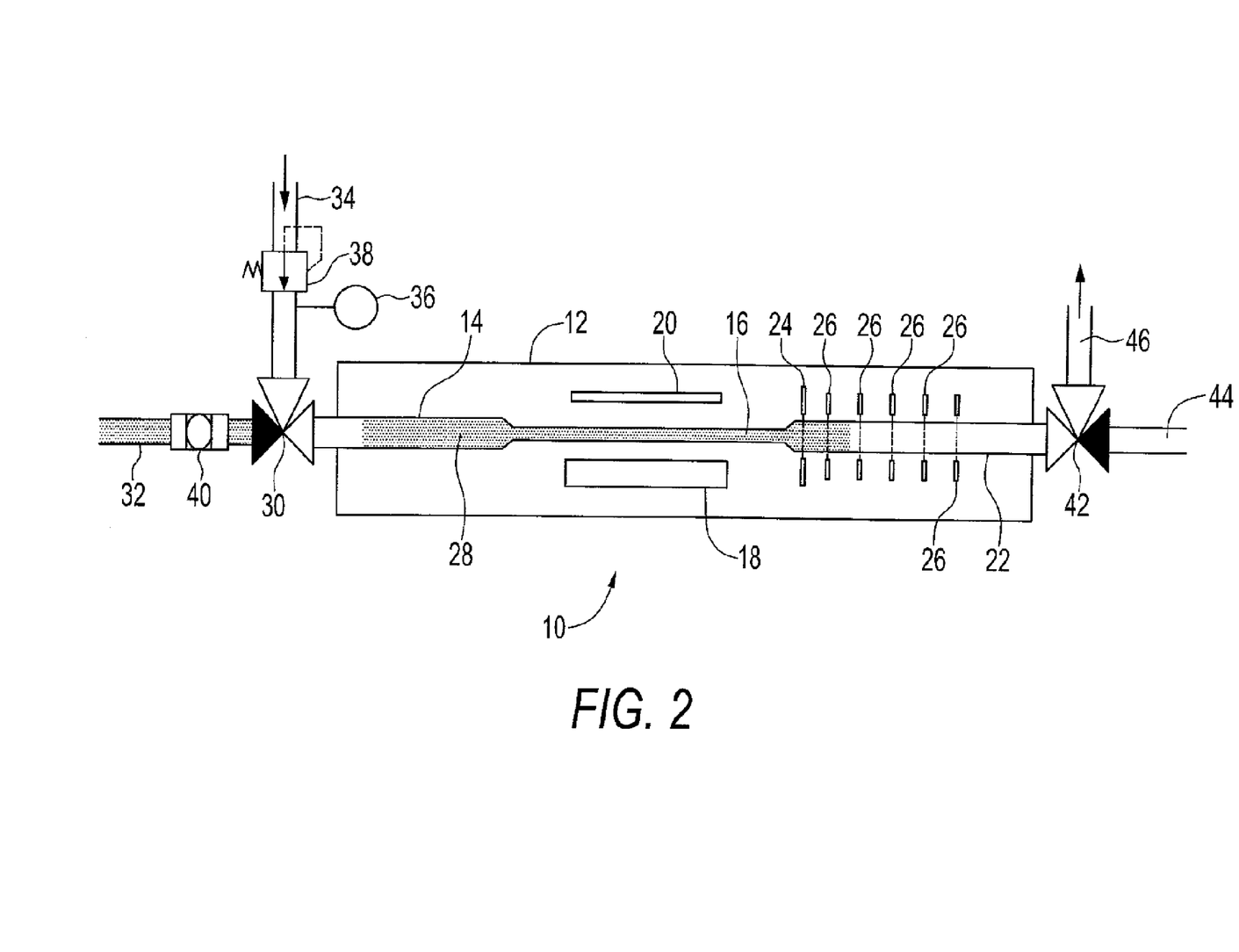
FIG. 2 is a side view of a viscometer according to the present invention.
Figure 3:
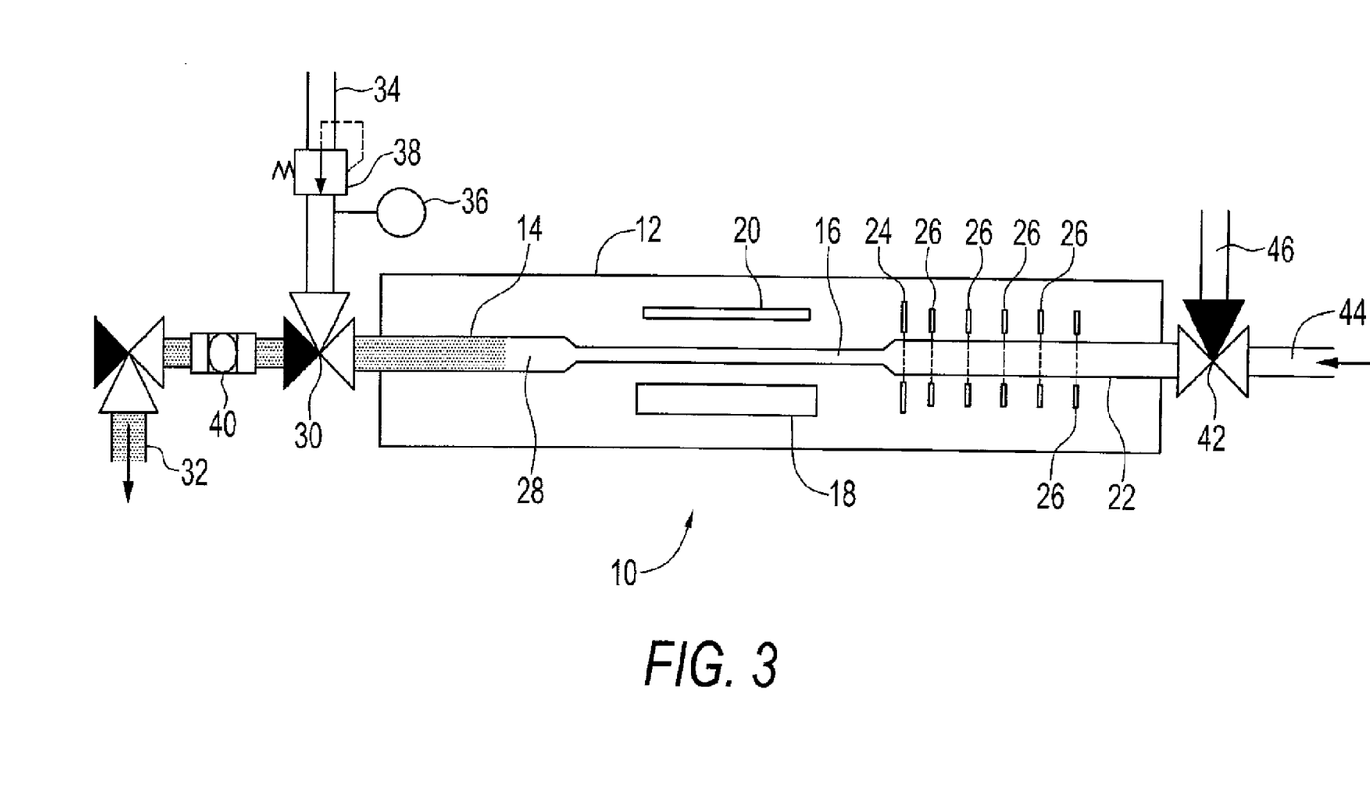
FIG. 3 is a side view of a viscometer according to the present invention.
Figure 4:
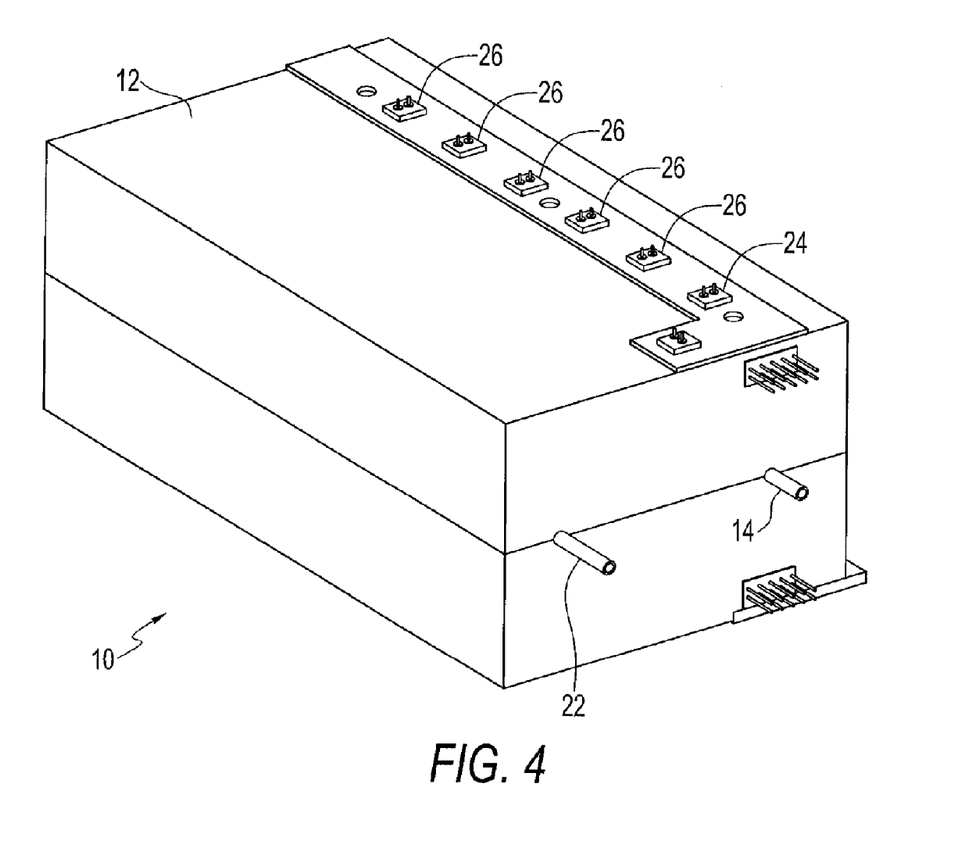
FIG. 4 is a perspective view of a viscometer according to the present invention.
Figure 5:
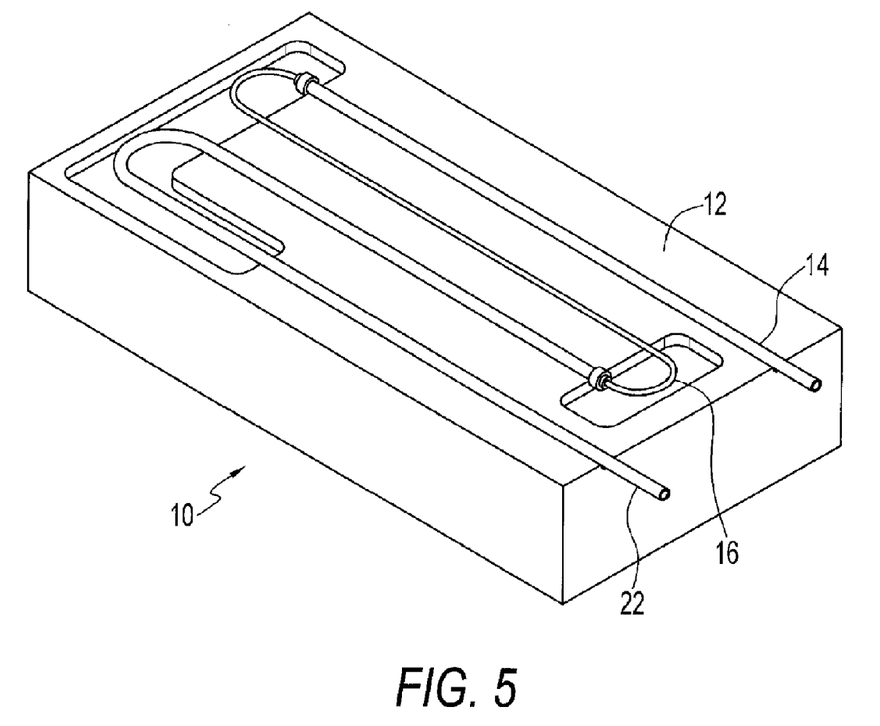
FIG. 5 is a perspective cut-away view of a viscometer according to the present invention.
Figure 6:
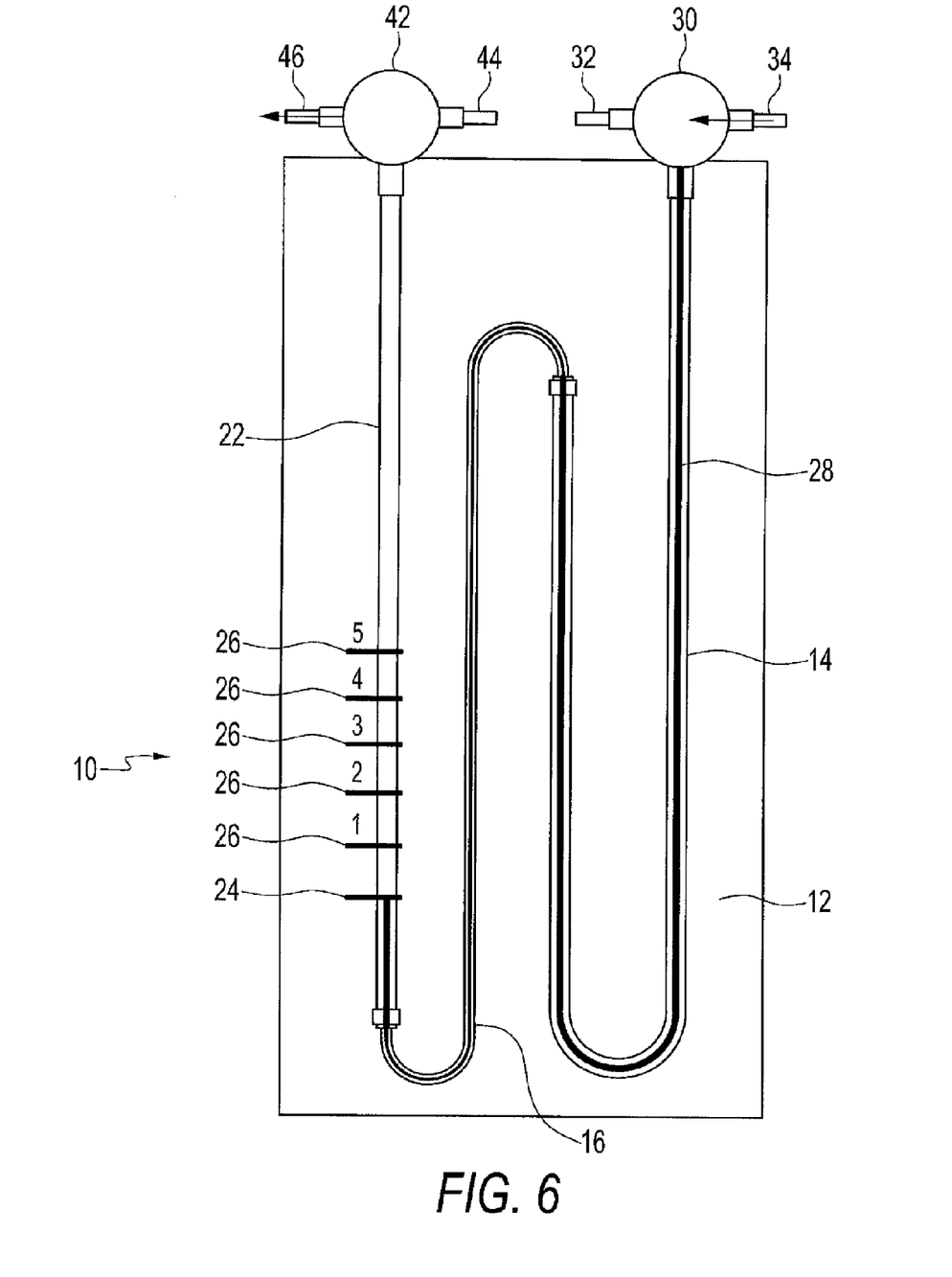
FIG. 6 is a top view of a viscometer according to the present invention.
Figure 7:
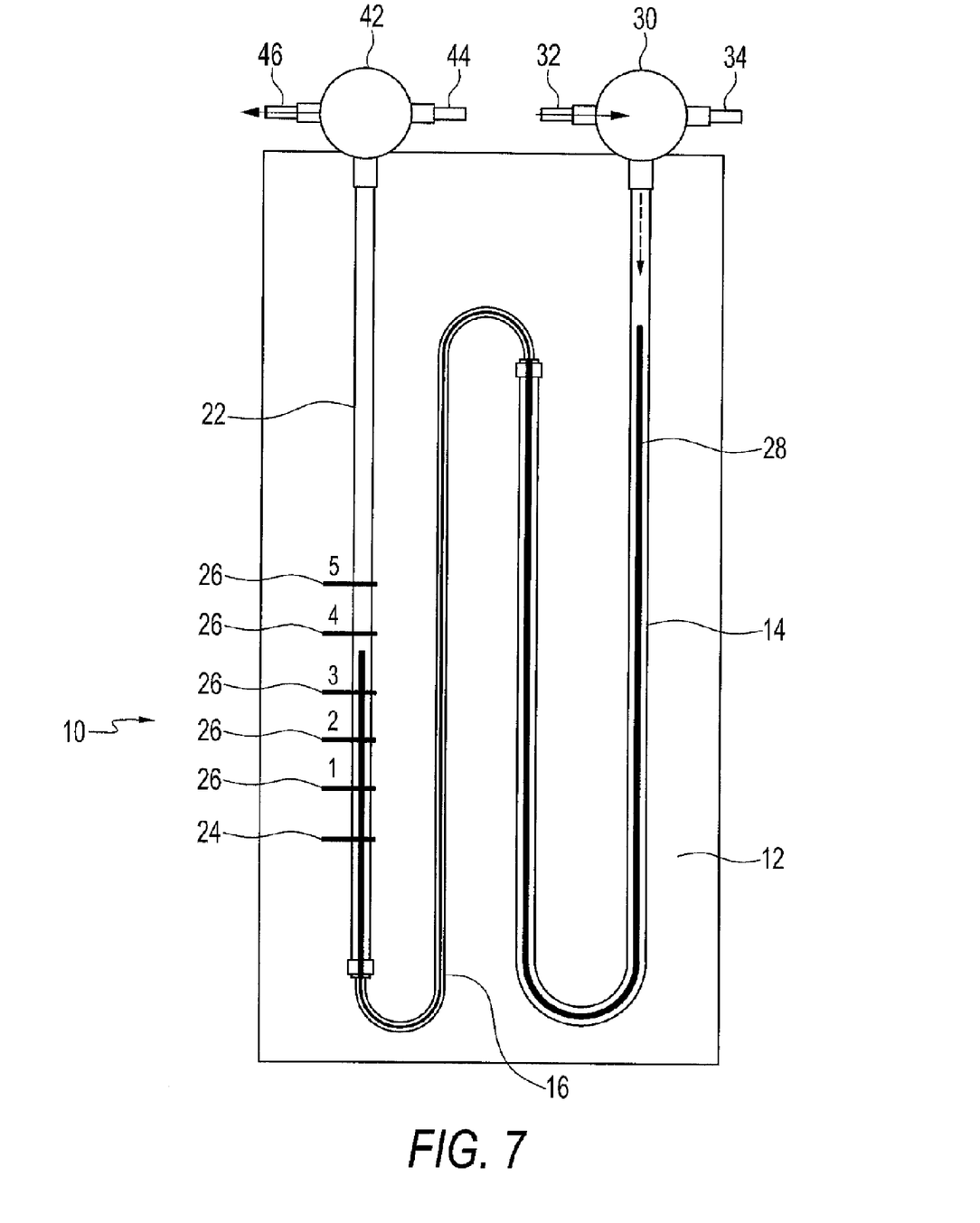
FIG. 7 is a top view of a viscometer according to the present invention.

The basic physical concept of the viscometer of the present invention is shown in FIGS. 1–7. The main components of the viscometer 10 are a thermal block 12, an entrance tube 14, capillary tube 16, thermo device 18, temperature sensor 20, velocity tube 22, start sensor 24 and flow sensors 26. FIGS. 1–3 show a side view of the operational stages of the viscometer 10. FIG. 4 shows a three-dimensional view of the viscometer 10. FIG. 5 shows a three-dimensional cut-away view of the viscometer 10. FIGS. 6–7 show a top view of the operational stages of the viscometer 10. The dimensions of various components and their materials of construction may vary for the viscometer 10; but typical choices are described herein.

The heart of the viscometer 10 is the non-glass capillary tube 16 that is embedded in the thermally conductive thermal block 12. The capillary tube 16 is in thermal contact with the thermal block 12 to provide heat transfer to the test specimen 28. The thermal block 12 maintains a constant temperature environment for the capillary tube 16 and test specimen 28. In experiments, aluminum was used for the thermal block 12. The thermo device 18 and the temperature sensor 20 are embedded in the thermal block 12 to maintain a constant temperature. The thermo device 18 can be a heater or some type of thermoelectric device for heating and cooling. Fluoroplastic material was found to be a very good material for the capillary tube 16, because of its optical clarity and easy nature to clean. Fluoroplastic is a generic name of a group of polymers. A well-known example of fluoroplastic is Teflon, which is trademarked by Dupont. In experiments, PolyTetraFluoroEthylene (PTFE) was used for the capillary tube 16. The PTFE is flexible, so that it can be fitted snuggly into a groove of the thermal block 12 to achieve good contact and thus heat transfer. Unlike glass, differential thermal expansion and contraction of the thermal block 12 and the capillary tube 16 would not cause the fluorocarbon material of the capillary tube 16 to crack. An internal diameter of the capillary tube 16 of approximately 0.5 mm was found to be a good choice. Though, internal diameters in the ranges of 0.3 to 1.6 mm were experimented and work adequately.

To make test specimen 28 introduction easier and to ensure as sufficient supply of thermally equilibrated test specimen 28 to keep the capillary tube 16 filled during measurement, the entrance tube 14 having a larger diameter than the capillary tube 16 is positioned upstream of the capillary tube 16. The entrance tube 14 is embedded in the thermal block 12 and is connected to the capillary tube 16. The entrance tube 14 extends out of the thermal block 12 and provides a path to the capillary tube 16. The entrance tube 14 used in experiments was approximately 1.6 mm internal diameter. The entrance tube 14 was made of the fluorocarbon Fluorinated Ethylene Propylene (FEP), which is another fluoroplastic.

The velocity tube 22 is of a larger diameter than the capillary tube 16 and is positioned downstream of the capillary tube 16. The velocity tube 22 is embedded in the thermal block 12 and is connected to the capillary tube 16. The velocity tube 22 extends out of the thermal block 12 and provides a path to the capillary tube 16. The velocity tube 22 in experiments was approximately 1.6 mm internal diameter. The most important function of the velocity tube 22 is to slow down the flow of the test specimen 28, thus allowing a more precise measurement of flow time. It is also easier to place flow sensors 26 against the larger velocity tube 22 than the capillary tube 16, because there is more space available and greater allowance for alignment of the flow sensors 26. The velocity tube 22 was also made of FEP. The diameters of the entrance tube 14 and velocity tube 22 should preferably be the same, so that the magnitude of pressure drop is preserved during flow of the test specimen 28 out of the entrance tube 14 and into the velocity tube 22. Otherwise, the flow of the test specimen 28 would not be steady and become a source of imprecision.

A three-way entrance valve 30 connected to the entrance tube 14 is shown in FIGS. 1–3 and 6–7. The entrance valve 30 allows the entrance tube 14 to be either connected to a source 32 of the test specimen 28 or to a source 34 of compressed gas. The compressed gas is maintained at a constant pressure during measurement and is used to drive or push the test specimen 28 through the capillary tube 16. Air was used as the compressed gas. A pressure sensor 36 before the entrance valve 30 is useful for monitoring the drive pressure during measurement of viscosity to allow comparison with the set-point pressure. The set-point pressure is the targeted operational drive pressure for the measurement process. If there is a difference between the actual pressure and the set-point pressure, a correction can be applied to the viscosity calculation to improve precision. A pressure regulating device 38 before the pressure sensor 36 is used to control the drive pressure. The strength of the drive pressure can be varied by adjusting the pressure regulating device 38. Different drive pressures will cause different shear rates in the test specimen. For Newtonian and laminar flow, the shear rate $\gamma$ at the walls of the capillary tube 16 can be shown to be directly proportional to drive pressure as $\gamma = \Delta PD/4 \mu L$. Where L and D are the length and internal diameter of the capillary system respectively, $\mu$ is the dynamic viscosity and $\Delta P$ is the drive pressure. Changing the shear rate is useful in characterizing the viscous behavior of non-Newtonian liquids. Since some test specimens 28 may contain dirt particles, it is useful to install a filter 40 between the source 32 of the test specimen 28 and the entrance valve 30 to prevent blockage of the capillary tube 16. The filter 40 would not be needed for clean test specimens 28, but the filter 40 allows both clean and unclean test specimens 28 to be tested by the viscometer 10.

FIGS. 1–3 and 6–7 show a 3-way vent valve 42 connected to the velocity tube 22. The vent valve 42 allows the velocity tube 22 to be either connected to a source 44 of pressurized cleaning media or to a vent 46. The vent valve 42 is opened to the vent 46 during viscosity measurement. At the end of the measurement, the vent valve 42 is connected to the source 44 of pressurized cleaning media for cleaning.

There are multiple flow sensors 26 positioned along the velocity tube 22 at well-defined distances. The distance between two consecutive flow sensors 26 is defined as one timing segment. The start sensor 24 is positioned before the first flow sensor 26 to sense when the test specimen 28 is at the velocity tube 22. The start sensor 24 and five flow sensors 26 forming four timing segments are show in FIGS. 1–3 and 6–7. In experiments, optical sensors each paired with a light emitter were used for the start sensor 24 and flow sensors 26. Infra-red detectors were also found to be effective. Instead of mounting the optical sensors/light emitters in close proximity to the velocity tube 22, one can also mount them more remotely and transmit the light signal with light fibers. Alternatively, thermal sensors can also be used to monitor the velocity of test specimen 28. The thermal sensor detects the difference in heat capacity between empty and filled conditions of the velocity tube 22.

The six pairs of optical sensors/light emitters are used to monitor the motion of the leading meniscus of the test specimen 28, specifically to measure the arrival time of the leading meniscus at the start sensor 24 and each flow sensor 26. Therefore, the velocity obtained by measuring the flow time across a timing segment can be correlated to the dynamic viscosity. The viscometer 10 should first be calibrated by testing standard samples with known viscosities. Knowing the flow time and the viscosity of the standard sample, one can calculate a calibration constant, which can then be applied to the dynamic viscosity calculation of unknown test specimens. A separate measurement of density of the test specimen 28 using a commercially available density meter allows the kinematic viscosity to be calculated. To calculate dynamic viscosity, only the flow time of one timing segment would be needed. But, having more than one timing segment permits multiple independent measurements of dynamic viscosity in one pass. This is helpful in establishing repeatability of the measurement in one test sequence. For example, experiments can be conducted in such a way that viscosities are calculated on a real time basis as the liquid of the test specimen 28 travels past the flow sensors 26. As soon as the flow times between consecutive timing segments are deemed to be sufficiently repeatable, the experiment is terminated. The earliest that this condition can be satisfied is after the leading meniscus has passed the third flow sensor 26, thus providing flow times over two timing segments. In such a procedure, one would not have to wait for the test specimen 28 to pass through all the remaining timing segments before the experiment is terminated, thus saving analysis time. On the other hand, the test specimen 28 can continue to flow past subsequent timing segments, if the initial two timing segments results are deemed not sufficiently repeatable, thereby allowing an opportunity for precision to improve.

FIG. 3 shows the cleaning cycle, where pressurized air or inert gas is first introduced into the velocity tube 22 by way of the vent valve 42 from source 44 to move the test specimen 28 backwards into the source 32 of the test specimen 28. The source 32 of the test specimen 28 can be replaced before the cleaning cycle with a waste receptacle. Also a valve to switch between the source 32 of the test specimen 28 and a waste receptacle can be installed before the entrance valve 30. Solvent is then forced into the velocity tube 22 from source 44 to clean the velocity tube 22, the capillary tube 16 and the entrance tube 14. After that, air or dry gas is introduced through the same path from source 44 to dry the velocity tube 22, the capillary tube 16 and the entrance tube 14. The alternate introduction of drying gas and solvent may be repeated to ensure thorough cleaning and drying of the velocity tube 22, the capillary tube 16 and the entrance tube 14. More than one type of solvent may be used to facilitate cleaning. Typically, a higher boiling solvent such as toluene is used first to clean. Next a lower boiling solvent such as petroleum ether or acetone is used to facilitate complete evaporation of the solvent and drying of the viscometer 10. After the viscometer 10 is thoroughly cleaned, it is ready for another measurement. Cleaning is critical in ensuring test precision.

A general method of use of the above described viscometer 10 is as follows. First, begin the test with a clean viscometer 10. Next, the viscometer 10 should first be calibrated using a minimum of one standard sample with known viscosity. The viscosity value of the standard sample should preferably be similar to that of the unknown test specimen 28 to be tested later. Based on the flow time and the viscosity of the standard sample, a calibration constant is obtained by dividing viscosity with flow time. Using the flow time measured for the unknown sample, the viscosity is calculated by multiplying flow time of the unknown test specimen 28 with the calibration constant obtained in measurement of the standard sample. The calibration procedure is the same as the following procedure for testing for the unknown viscosity of a test specimen 28.

As shown in FIGS. 1 and 6, deliver the test specimen 28 to the start sensor 24 by either pushing the test specimen 28 from behind with the compressed gas or pulling the test specimen 28 with a vacuum attached to the vent 46. After the test specimen 28 has arrived at the position of the start sensor 24, the flow of the test specimen 28 is temporarily stopped to allow the test specimen 28 to equilibrate to a temperature in the thermal block 12. The flow is stopped by turning off the pressure or vacuum moving the test specimen 28. One-hundred-and-fifty seconds of time was used in experiments to allow for the temperature of the test specimen 28 to equilibrate in the thermal block 12. The time for temperature equilibration is dependant on the heat transfer characteristics of the test specimen 28. At the end of the equilibration period, the entrance valve 30 is switched to allow the compressed gas to enter the entrance tube 14 and push the test specimen 28 forward at a fixed pressure, as shown in FIGS. 2 and 7. Simultaneously, the vent valve 42 is switched to the vent position, when the entrance valve 30 is switched to the source 34 of the compressed gas. One to ten psig gas pressure for the drive pressure was used in experiments. Although, using compressed gas to push the test specimen 28 is the optimum way to move the test specimen 28, the test specimen 28 could also be continued to be pulled through the velocity tube 22 by a vacuum attached to the vent 46.

The flow sensors 26 placed along the flow path of the velocity tube 22 monitor the passing of the leading meniscus of the test specimen 28. The time it takes to travel between a timing segment is called the "flow time". Multiple flow times are collected as the test specimen 28 travels past more than one timing segment. Each flow time measurement allows the dynamic viscosity to be calculated. With multiple flow times available, measurement repeatability can be calculated. Once a satisfactory repeatability is achieved, the test can be terminated. If desired, the test can also be terminated after the leading meniscus has passed the last timing segment. The procedure of using all the timing segments would take a longer time, but provides more data to establish statistical significance. At the end of a test, both the entrance valve 30 and the vent valve 42 are switched as shown in FIG. 3 to allow air, followed by solvent(s) from the source 44 to clean and dry the entrance tube 14, capillary tube 16 and velocity tube 22 in a back-flushing manner. It was found that using alternate bursts of solvent and air was more effective in cleaning the viscometer 10 than using continuous streams of each of the cleaning media, probably because of increased agitation and mixing. Once the entrance tube 14, capillary tube 16 and exit tube 22 have been cleaned and dried, the viscometer 10 is ready for another measurement.

Figure 8:
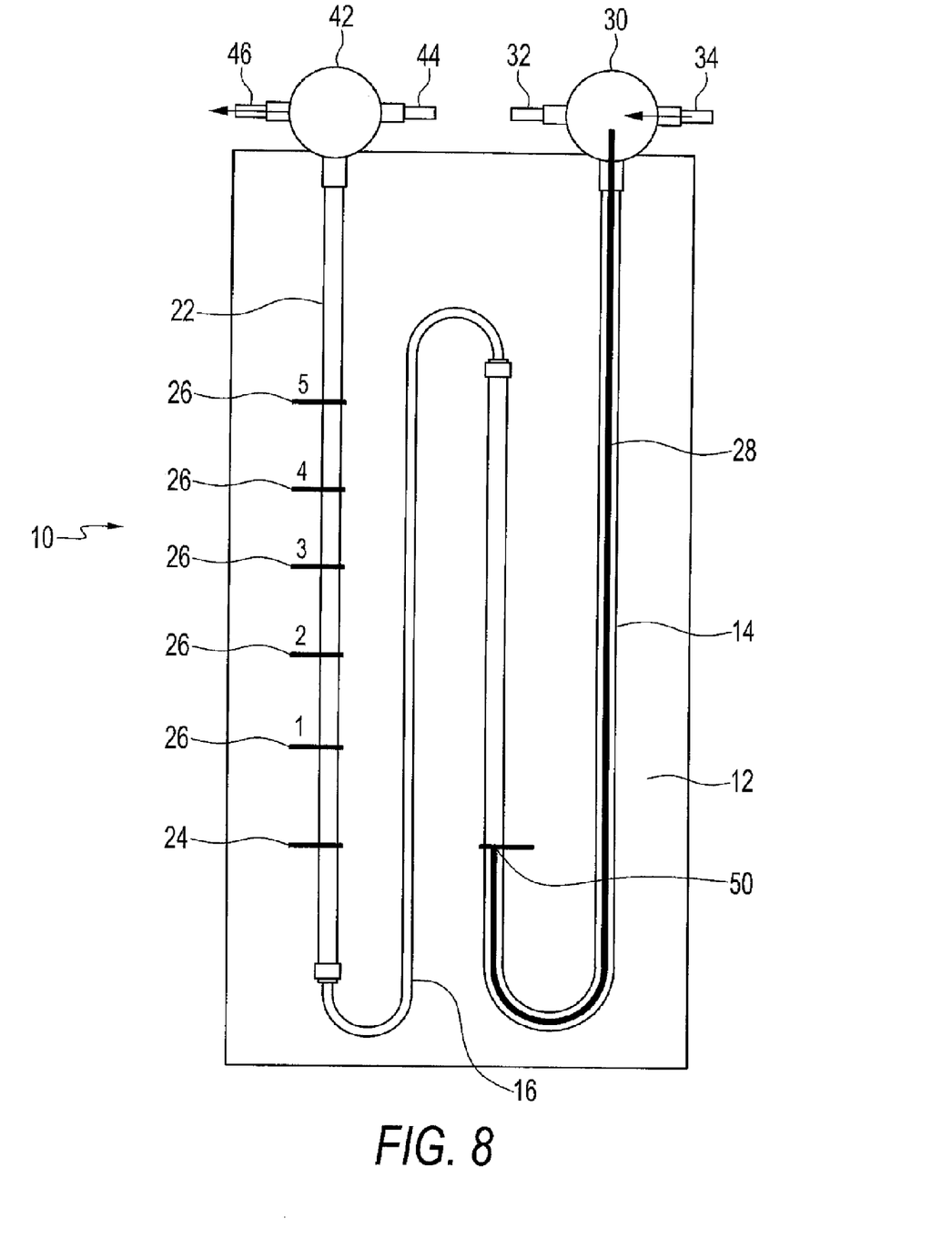
FIG. 8 is a top view of a viscometer according to the present invention.
Figure 9:
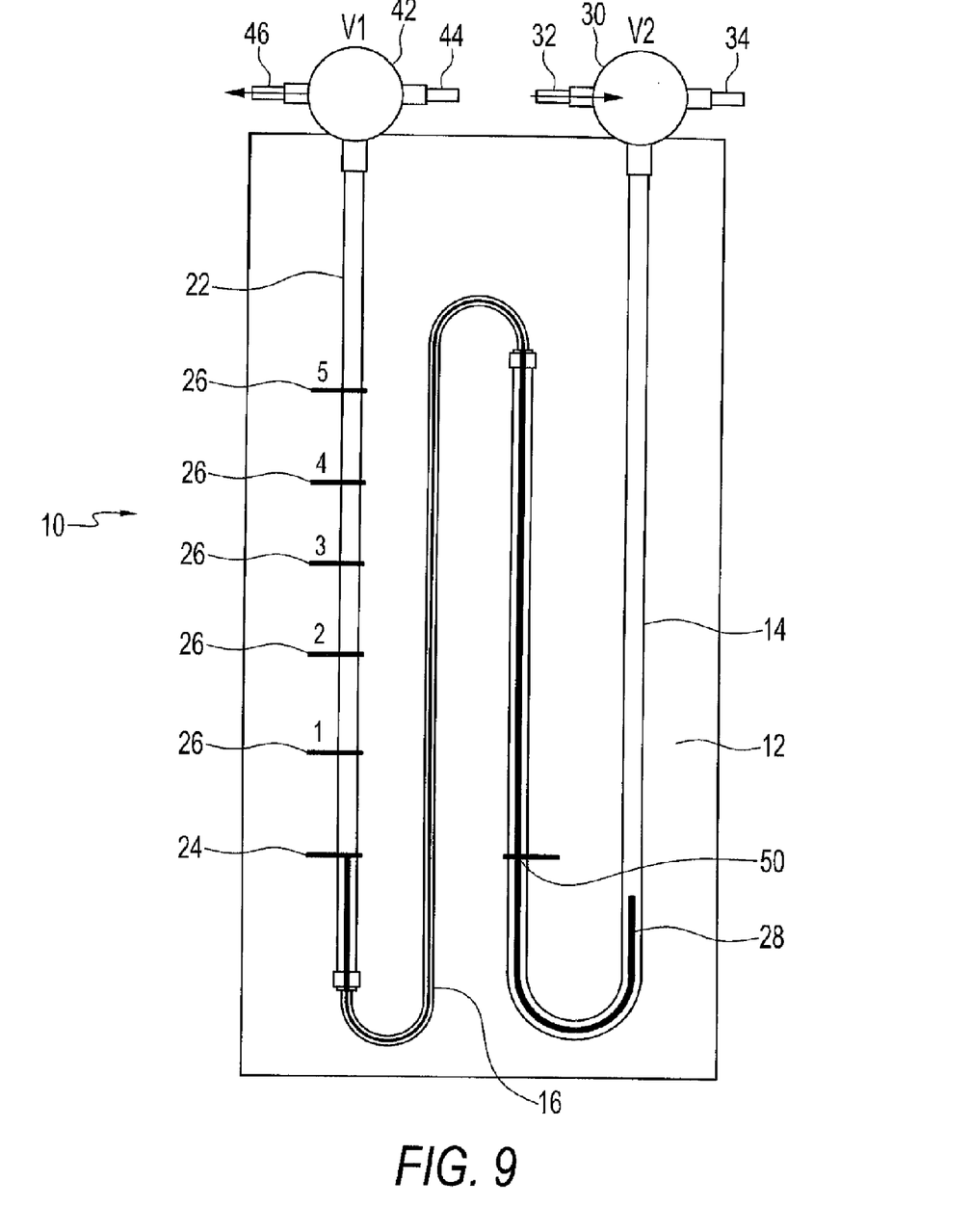
FIG. 9 is a top view of a viscometer according to the present invention.
Figure 10:
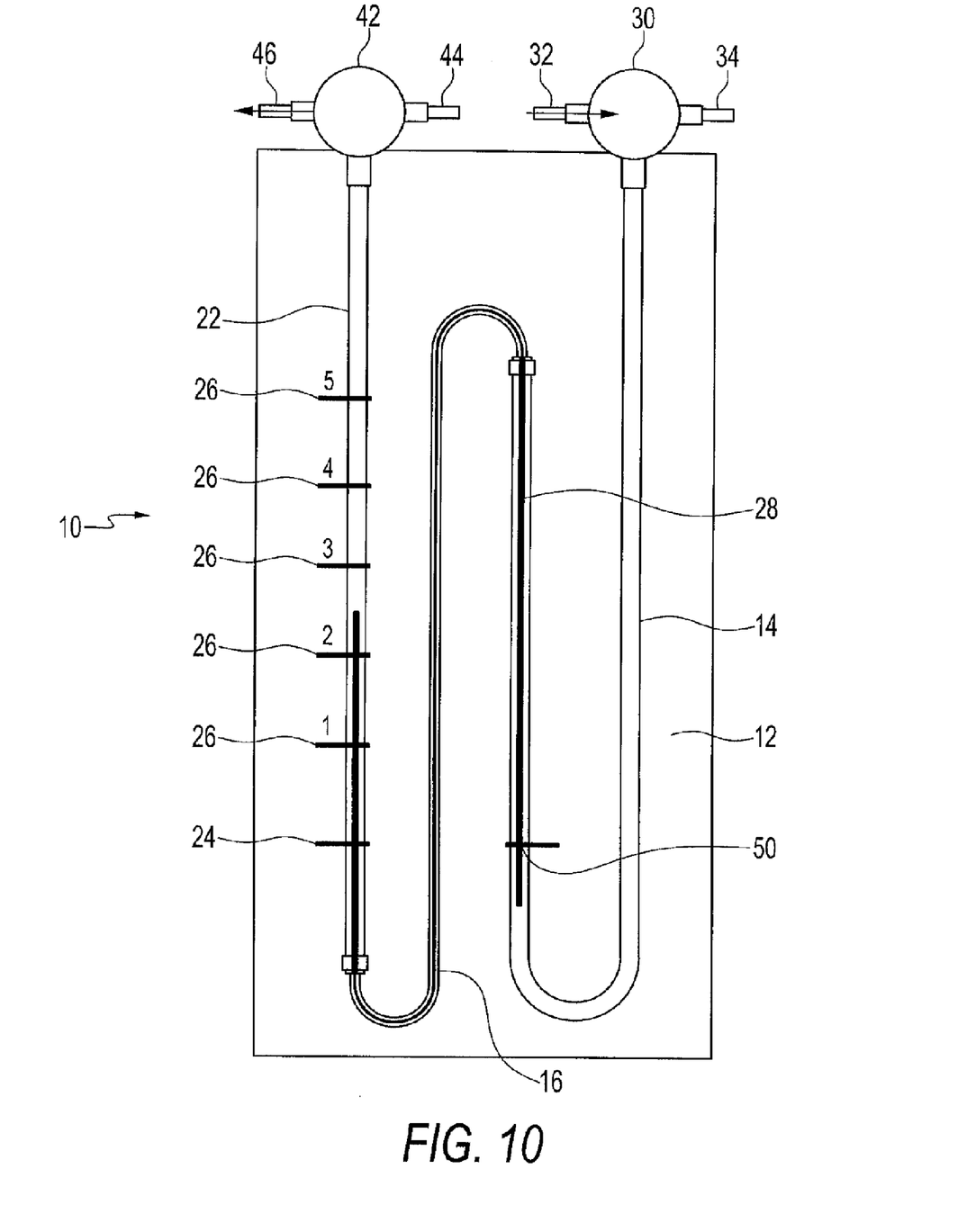
FIG. 10 is a top view of a viscometer according to the present invention.
Figure 11:
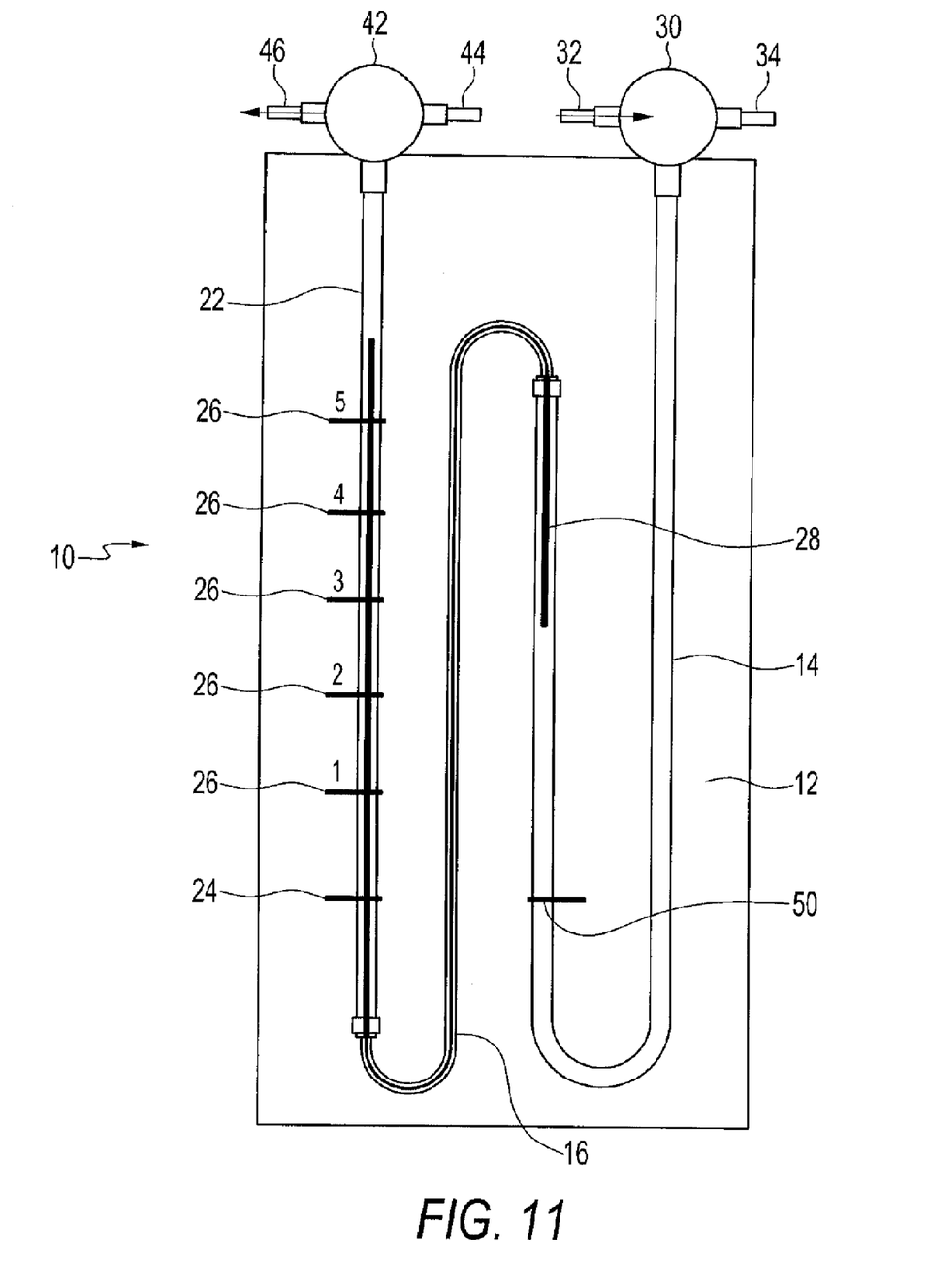
FIG. 11 is a top view of a viscometer according to the present invention.

An alternative version of the viscometer 10 allows for improved precision. Since the entrance valve 30 cannot be conveniently installed inside the thermal block 12 without sacrificing a compact design, a very small amount of test specimen 28 which resides inside the entrance valve 30 is not heated or cooled by the thermal block 12 during the equilibration period. This small amount of liquid, which typically represents less than 1% of the total sample volume, is pushed through the thermal block 12 during measurement. The lack of temperature equilibrium for this small amount of the sample has a minor effect on viscosity results. However, even this minor problem can be mitigated by installing an additional flow sensor 50 upstream of the capillary tube 16 as shown in FIGS. 8–11. The test procedures are similar to the those described earlier, except for the following differences, which are shown in FIG. 8–11. The test specimen 28 is delivered to a fill position at flow sensor 50, thereby changing the starting mark from the start sensor 24 to the additional flow sensor 50, as shown in FIG. 8. The flow sensor 50 is positioned before the start sensor 24. The entrance valve 30 and vent valve 42 are switched to allow the compressed gas to enter and push the test specimen 28 forward until the leading meniscus reaches the start sensor 24, as shown in FIG. 9. After the test specimen 28 has arrived at the position of the start sensor 24 the flow is temporarily stopped to allow the test specimen 28 to equilibrate to the temperature in the thermal block 12. The method of the measurement process is then the same from this point on, as described above for the general method and shown in FIGS. 10 and 11. In this manner, all of the test specimen 28 resides in the thermal block and is equilibrated to the same target temperature.

The viscometer 10 of the present invention provides the following advantages due to the use of fluoroplastic materials instead of glass. The capillary tube 16 is flexible as opposed to glass and can be curved and bent to make the viscometer 10 more compact, as shown in FIGS. 4–5. FIG. 4 shows a PCB board of light emitters and PCB board of optical sensors. The fluoroplastic materials are not fragile like glass. The fluoroplastic materials are much easier to clean than glass because of its slippery surface. Glass is vulnerable to permanent, scouring damage caused by turbulent flow of solvent and air. A fluoroplastic tube is much cheaper than the glass capillary of D445 standard that requires special blown glass with timing bulbs and intricate shapes. Similar to glass, certain fluoroplastic provides optical clarity to allow optical measurement of meniscus movement. However, it should be noted that other means of meniscus detection that does not rely on optical signal is also workable. Also, the entire tube does not have to be made of fluoroplastic, as a fluoroplastic coating on tubes made of other materials would also work as long as the other material characteristics required for the measurement are met. Other plastic tubes may also be used as long as they possess the beneficial characteristics of fluoroplastic such as slippery surface, chemical and temperature resistance.

Changing the shear rate of the test provides useful information about the test specimen 28. The viscometer 10 allows a convenient means of changing shear rate by changing the pressure of the driving gas and/or the internal diameter of the capillary tube. The D445 standard relies solely on gravitational force to drive the sample and therefore does not have the flexibility of changing shear rate using other motive forces, unless the glass tube is replaced with another one that has a different internal diameter. Changing a glass capillary is a cumbersome and delicate procedure. Also, one has to wait for the glass capillary to achieve temperature equilibrium with the bath after the tube change. This usually takes several hours. Finally, the viscometer 10 of the present invention is amenable to a continuous numerical modification of the shear rate by varying the drive pressure, whereas changes in shear rate in D445 standard can only be practically achieved in finite discrete steps with different sizes of glass tubes. It should also be noted that the viscometer 10 can be orientated such that the fluoroplastic tube is positioned vertically to allow the force of gravity to move the test specimen 28. The flow time from this setup can be used to correlate to the kinematic viscosity of the test specimen 28. In this way, there is no need to measure density in order to calculate kinematic viscosity; however, the trade-off of this setup is that the dynamic viscosity value cannot be obtained.

Use of a solid thermal block 12 extends the range of temperature in which the viscometer 10 can be used. The operating range of liquid bath is limited by the boiling point, freezing point and viscosity of the bath liquid. This is especially true for a bath having a high viscosity under low temperature. Also, use of the back-flushing technique during cleaning minimizes solvent consumption. If forward-flush were to be used, longer portions of the flow-path will be exposed to the test specimen 28, thus more solvent would be needed to clean it afterwards. Back-flushing also facilitates cleaning of the filter 40, as dirt particles are more easily dislodged by the reverse flow and eliminating the need for manual cleaning of the filter 40. In summary, the viscometer 10 of the present invention allows viscosity measurements in a more compact system, is safer in design, less costly to build, amenable to automatic cleaning, useable in a broader temperature range and finally, more versatile in providing viscosity data.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

What is claimed is:

1. A viscometer for testing the viscosity of a test specimen comprising:
   a thermal block;
   a thermo device to control temperature of said thermal block;
   a temperature sensor to sense temperature of said thermal block;
   a capillary tube embedded in said thermal block such that said capillary tube is in thermal contact with said thermal block;
   an entrance tube connected to said capillary tube and embedded in said thermal block, said entrance tube providing a pathway to said capillary tube from outside said thermal block;
   a velocity tube connected to said capillary tube and embedded in said thermal block, said velocity tube providing a pathway to said capillary tube from outside said thermal block; and
   at least two flow sensors aligned along said velocity tube adapted to measure velocity of the test specimen in said velocity tube.

2. The viscometer of claim 1, wherein said entrance tube is larger than said capillary tube adapted to provide easy entrance of the test specimen and ensure a sufficient supply of thermally equilibrated test specimen to keep said capillary filled during measurement.

3. The viscometer of claim 1, wherein said velocity tube is larger than said capillary tube adapted to provide a slow down effect for entrance of the test specimen into said velocity tube.

4. The viscometer of claim 1, further including a vent source, a cleaning source and an vent valve to attached to said velocity tube, said vent valve also attached to said vent source and said cleaning source such as to allow switching access to said velocity tube between said vent source and said cleaning source.

5. The viscometer of claim 1, further including a compressed gas source connected to said entrance tube.

6. The viscometer of claim 1, further including a start sensor positioned to detect the test specimen at a start position prior to said at least two flow sensors.

7. The viscometer of claim 6, further including an additional flow sensor upstream of said capillary tube and said start sensor.

8. The viscometer of claim 1, wherein said entrance tube, capillary tube and velocity tubes have an inside surface made of an easily cleaned material.

9. The viscometer of claim 8, wherein said easily cleaned material is a fluoroplastic.

10. The viscometer of claim 1, further including a test specimen source, a compressed gas source and an entrance valve to attached to said entrance tube, said entrance valve also attached to said test specimen source and said compressed gas source such as to allow switching access to said entrance tube between said test specimen source and said compressed gas source.

11. The viscometer of claim 10, further including a vent source, a cleaning source and an vent valve to attached to said velocity tube, said vent valve also attached to said vent source and said cleaning source such as to allow switching access to said velocity tube between said vent source and said cleaning source.

12. The viscometer of claim 1, further including a cleaning source connected to said velocity tube.

13. The viscometer of claim 12, wherein internal diameters of said entrance and velocity tubes are the same to ensure steady flow of the test specimen.

14. The viscometer of claim 1, wherein said entrance tube is larger than said capillary tube adapted to provide easy entrance of the test specimen; wherein said velocity tube is larger than said capillary tube adapted to provide a slow down effect for entrance of the test specimen into said velocity tube; wherein said entrance tube, capillary tube and velocity tubes have an inside surface made of an easily cleaned material; further including a test specimen source, a compressed gas source and an entrance valve to attached to said entrance tube, said entrance valve also attached to said test specimen source and said compressed gas source such as to allow switching access to said entrance tube between said test specimen source and said compressed gas source; and further including a vent source, a cleaning source and an vent valve to attached to said velocity tube, said vent valve also attached to said vent source and said cleaning source such as to allow switching access to said velocity tube between said vent source and said cleaning source.

15. The viscometer of claim 14, wherein said velocity tube is of a clear material and said at least two flow sensors are paired optical sensors and light emitters.

16. The viscometer of claim 14, wherein said easily cleaned material is a fluoroplastic.

17. The viscometer of claim 16, wherein said velocity tube is of a clear material and said at least two flow sensors are paired optical sensors and light emitters.

18. The viscometer of claim 14, further including a start sensor positioned to detect the test specimen at a start position prior to said at least two flow sensors.

19. The viscometer of claim 18, further including an additional flow sensor upstream of said capillary tube and said start sensor.

20. A method of measuring viscosity of a test specimen using a viscometer including a thermal block, a capillary tube embedded in the thermal block such that the capillary tube is in thermal contact with the thermal block, an entrance tube connected to the capillary tube and embedded in the thermal block with the entrance tube providing a pathway to the capillary tube from outside the thermal block, a velocity tube connected to the capillary tube and embedded in the thermal block with velocity tube providing a pathway to the capillary tube from outside the thermal block, at least two consecutive flow sensors aligned along the velocity tube to measure velocity of the test specimen in the velocity tube, comprising:
   beginning with an empty viscometer;
   delivering the test specimen to the connection of the capillary tube and the velocity tube by pushing the test specimen from behind with compressed gas through the entrance tube and the capillary tube;
   temporarily stopping flow of the test specimen to allow the test specimen to equilibrate to a target temperature in the thermal block, whereby temperature of the thermal block is controlled by a thermal device;
   once the temperature of the test specimen is equilibrated, allowing the compressed gas to push the test specimen forward into the velocity tube at a fixed pressure while simultaneously venting the velocity tube from outside the thermal block;
   using the flow sensors placed along the flow path of the velocity tube to monitor passing of a leading meniscus of the test specimen; and
   recording time it takes a leading meniscus of the test specimen to travel between the at least two consecutive flow sensors to determine velocity of the flow between the at least two consecutive flow sensors.

21. The method of claim 20, using a start sensor at the connection of the velocity tube and capillary to determine when the leading meniscus of the test specimen reaches that connection in order to stop the flow and allow the test specimen to equilibrate to the temperature of the thermal block.

22. The method of claim 20, substituting pushing the test specimen with the compressed gas with pulling the test specimen with a vacuum attached to the velocity tube.

23. The method of claim 20, further including changing the shear rate of the test specimen by changing the pressure of the compressed gas pushing the test specimen.

24. The method of claim 20, wherein said entrance tube, capillary tube and velocity tubes have an inside surface made of an easily cleaned material.

25. The method of claim 20, wherein said easily cleaned material is a fluoroplastic.

26. The method of claim 20, further including connecting the velocity tube to a cleaning source and connecting the entrance tube to a test specimen receptacle; introducing a pressurized gas into the velocity tube to move the test specimen backwards into the test specimen receptacle by way of the capillary tube and entrance tube; forcing a solvent into the velocity tube towards the capillary tube to clean the velocity tube, the capillary tube and the entrance tube; and introducing a drying gas through the same path as the solvent to dry the velocity tube, the capillary tube and the entrance tube.

27. The method of claim 26, further including alternate introduction of drying gas and solvent in a repeated sequence to ensure thorough cleaning and drying of the velocity tube, the capillary tube and the entrance tube.

28. The method of claim 20, further including calibrating the viscometer using at least one standard sample with a known viscosity by determining the time it takes the standard sample travel between consecutive flow sensors in the viscometer and determine a calibration constant based on the time and the viscosity of the standard sample by dividing viscosity with the time and further calculating the viscosity of the test specimen by multiplying flow time of the test specimen with the calibration constant.

29. The method of claim 28, wherein viscosity value of the standard sample is similar to that of the unknown test specimen.

* * * * *